(12) United States Patent
Hansen et al.

(10) Patent No.: US 12,257,428 B2
(45) Date of Patent: Mar. 25, 2025

(54) SYSTEMS AND METHODS FOR WIRELESS ENERGY TRANSFER FOR VENTRICULAR ASSIST DEVICES

(71) Applicant: TC1 LLC, St. Paul, MN (US)

(72) Inventors: John Freddy Hansen, Pleasanton, CA (US); Eric Lee, Oakland, CA (US)

(73) Assignee: TC1 LLC, St. Paul, MN (US)

( * ) Notice: Subject to any disclaimer, the term of this patent is extended or adjusted under 35 U.S.C. 154(b) by 558 days.

(21) Appl. No.: 17/197,518

(22) Filed: Mar. 10, 2021

(65) Prior Publication Data

US 2021/0283391 A1    Sep. 16, 2021

Related U.S. Application Data

(60) Provisional application No. 62/987,468, filed on Mar. 10, 2020.

(51) Int. Cl.
*A61M 60/873* (2021.01)
*A61M 60/178* (2021.01)
(Continued)

(52) U.S. Cl.
CPC ........ *A61M 60/873* (2021.01); *A61M 60/178* (2021.01); *A61M 60/876* (2021.01);
(Continued)

(58) Field of Classification Search
CPC .............. A61M 60/873; A61M 60/876; A61M 2205/04; A61M 60/216;
(Continued)

(56) References Cited

U.S. PATENT DOCUMENTS 9,415,149 B2    8/2016 Smith et al.
9,496,719 B2    11/2016 Kesler et al.
(Continued)

FOREIGN PATENT DOCUMENTS

CN    204538825 U  *  8/2015
CN    206180709 U      5/2017
(Continued)

OTHER PUBLICATIONS

A. L. F. Stein, P. A. Kyaw and C. R. Sullivan, "High-Q self-resonant structure for wireless power transfer," 2017 IEEE Applied Power Electronics Conference and Exposition (APEC), Tampa, FL, USA, 2017, pp. 3723-3729, doi: 10.1109/APEC.2017.7931234. (Year: 2017).*

(Continued)

*Primary Examiner* — Pamela M. Bays
*Assistant Examiner* — Christine Sison
(74) *Attorney, Agent, or Firm* — Armstrong Teasdale LLP (57) ABSTRACT

A wireless power transfer system is provided. The system includes an external transmit resonator and an implantable receive resonator. The transmit resonator is configured to transmit wireless power, wherein the external transmit resonator includes one of i) one or more loops of Litz wire and ii) a plurality of stacked plates. The implantable receive resonator is configured to receive the transmitted wireless power from the external transmit resonator, wherein the implantable receive resonator is configured to power a ventricular assist device (VAD) implanted in a subject using (Continued)

the received wireless power. The implantable receive resonator includes the other of i) the one or more loops of Litz wire and ii) the plurality of stacked plates.

17 Claims, 11 Drawing Sheets

(51) Int. Cl.
    *A61M 60/876*     (2021.01)
    *H02J 50/12*     (2016.01)
    *H02J 50/90*     (2016.01)

(52) U.S. Cl.
    CPC .......... *H02J 50/12* (2016.02); *A61M 2205/04* (2013.01); *H02J 50/90* (2016.02)

(58) Field of Classification Search
    CPC ...... A61M 2205/3613; A61M 2205/82; A61M 2205/8243; H02J 50/12; H02J 50/90; H02J 2310/23; H01F 27/2823; H01F 27/2866; H01F 27/2847; H01F 38/14
    See application file for complete search history.

(56) References Cited

U.S. PATENT DOCUMENTS

| | | | |
|---|---|---|---|
| 10,279,096 B2 | 5/2019 | Stark et al. | |
| 10,873,220 B2 | 12/2020 | Hansen et al. | |
| 2004/0097861 A1* | 5/2004 | Abe | A61M 60/113 604/4.01 |
| 2014/0031607 A1 | 1/2014 | Zilbershlag et al. | |
| 2017/0043077 A1* | 2/2017 | Tuseth | A61M 60/873 |
| 2017/0063143 A1 | 3/2017 | Hoarau et al. | |
| 2017/0216508 A1* | 8/2017 | Zilbershlag | H01F 38/14 |

FOREIGN PATENT DOCUMENTS

| | | | |
|---|---|---|---|
| EP | 3539613 A1 | 9/2019 | |
| IN | 201941023595 A | 12/2020 | |
| WO | 2013138451 A1 | 9/2013 | |
| WO | 2014121100 A1 | 8/2014 | |
| WO | WO-2016057525 A1 * | 4/2016 | ............. A61M 1/12 |
| WO | 2017025606 A1 | 2/2017 | |
| WO | 2018018006 A1 | 1/2018 | |
| WO | 2018222669 A1 | 12/2018 | |

OTHER PUBLICATIONS

International Search Report and Written Opinion for International Patent Application No. PCT/US2021/021628, mailed May 26, 2021, 16 pages.

Stein et al., "Thin Self-Resonant Structures with a High-Q for Wireless Power Transfer", Mar. 4, 2018, Thayer School of Engineering, Dartmouth College, Hanover, NH, 8 pages, accessed online at URL: https://cpb-us-e1.wpmucdn.com/sites.dartmouth.edu/dist/c/87/files/2017/12/Thin_Structure.pdf.

* cited by examiner

SYSTEMS AND METHODS FOR WIRELESS ENERGY TRANSFER FOR VENTRICULAR ASSIST DEVICES

CROSS-REFERENCE TO RELATED APPLICATIONS

This application claims priority to provisional application Ser. No. 62/987,468, filed Mar. 10, 2020, which is incorporated herein by reference in its entirety.

BACKGROUND OF THE DISCLOSURE a. Field of the Disclosure

The present disclosure relates generally to wireless power transfer systems, and more specifically relates to a wireless power transfer system used to power a ventricular assist device.

b. Background

Ventricular assist devices, known as VADs, are implantable blood pumps used for both short-term (i.e., days or months) and long-term (i.e., years or a lifetime) applications where a patient's heart is incapable of providing adequate circulation, commonly referred to as heart failure or congestive heart failure. A patient suffering from heart failure may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function.

A wireless power transfer system may be used to supply power to the VAD. Such power transfer systems generally include an external transmit resonator and an implantable receive resonator configured to be implanted inside a patient's body. One of the challenges is dissipation of the heat from the receive resonator to prevent an excessive rise of temperature inside a patient's body. Further, it is desirable for the wireless power transfer system to transmit power efficiently, as well as to be relatively easy to position within the patient's body.

SUMMARY OF THE DISCLOSURE

The present disclosure is directed to a wireless power transfer system. The system includes an external transmit resonator and an implantable receive resonator. The transmit resonator is configured to transmit wireless power, wherein the external transmit resonator includes one of i) one or more loops of Litz wire and ii) a plurality of stacked plates. The implantable receive resonator is configured to receive the transmitted wireless power from the external transmit resonator, wherein the implantable receive resonator is configured to power a ventricular assist device (VAD) implanted in a subject using the received wireless power. The implantable receive resonator includes the other of i) the one or more loops of Litz wire and ii) the plurality of stacked plates.

The present disclosure is further directed to a wireless power transfer system. The system includes an external transmit resonator configured to transmit wireless power. The system also includes an implantable receive resonator configured to receive the transmitted wireless power from the external transmit resonator. The implantable receive resonator is configured to be implanted in a thoracic cavity of a subject and configured to power a VAD implanted in the subject using the received wireless power.

The present disclosure is also directed to a method of transmitting wireless power. The method includes transmitting wireless power from an external transmit resonator to an implantable receive resonator, wherein the external transmit resonator includes one of i) one or more loops of Litz wire and ii) a plurality of stacked plates. The method further includes receiving the wireless power at the implantable receive resonator, wherein the implantable receive resonator includes the other of i) the one or more loops of Litz wire and ii) the plurality of stacked plates. The method also includes powering the VAD using the received wireless power.

The present disclosure is further directed to a method of transmitting wireless power. The method includes transmitting wireless power from an external transmit resonator to an implantable receive resonator. The method also includes receiving the wireless power at the implantable receive resonator implanted in a thoracic cavity of a subject implanted with a VAD, and powering the VAD using the received wireless power.

DETAILED DESCRIPTION OF THE DISCLOSURE

The present disclosure is directed to a wireless power transfer system. An implantable receive resonator of the wireless power transfer system is configured to be implanted in a thoracic cavity of the patient for improved dissipation of heat. In some embodiments, the power transfer system may be a hybrid system that uses a first resonator having loops of Litz wire with a second resonator having stacked plates.

Figure 1:
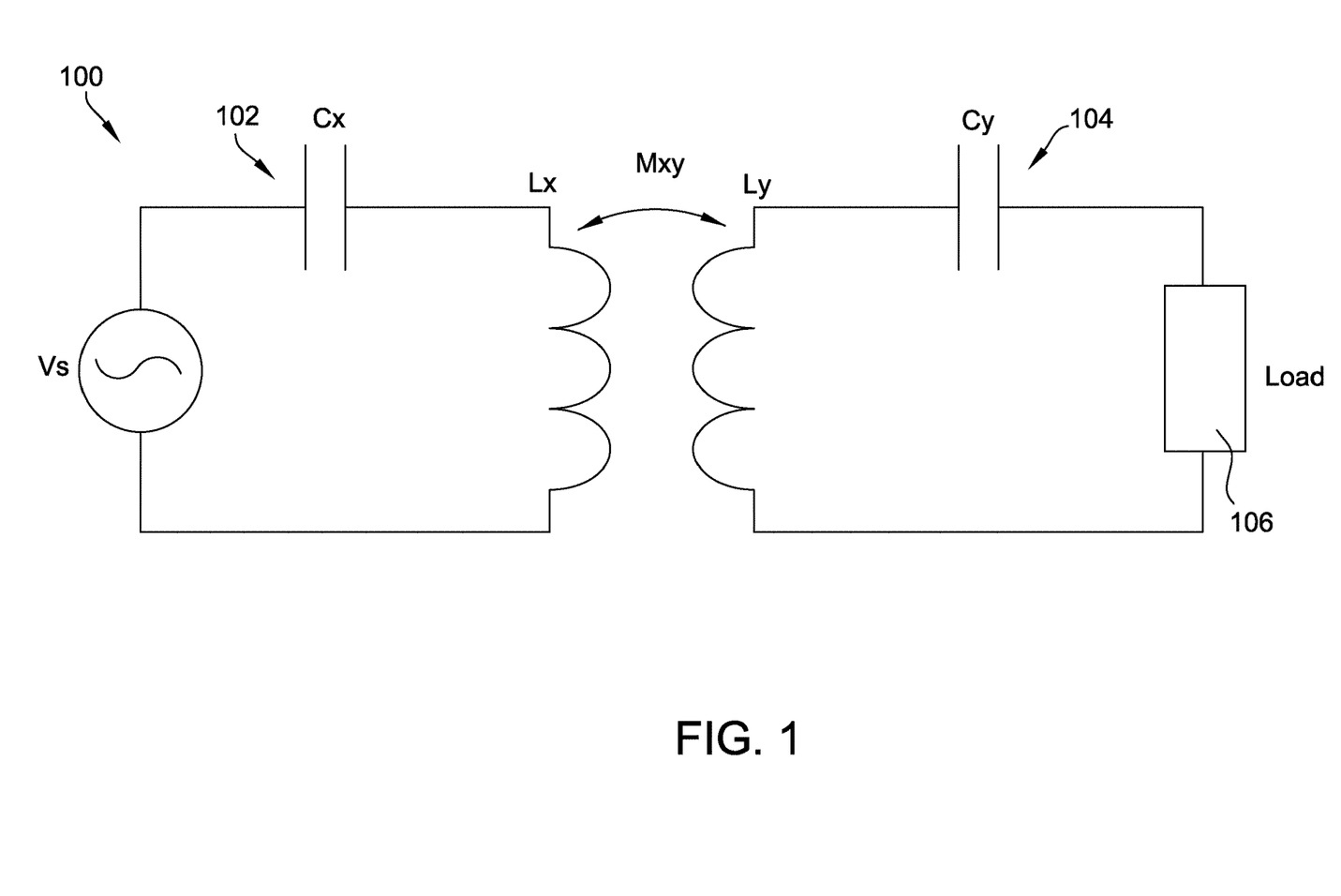
FIG. 1 is a simplified electrical circuit diagram of an exemplary wireless power transfer system.

Referring now to the drawings, FIG. 1 is a simplified electrical circuit diagram of an exemplary wireless power transfer system 100. The wireless power transfer system 100 includes an external transmit resonator 102 and an implantable receive resonator 104. The wireless power transfer system 100 shows a series connection where a capacitor Cx, Cy is electrically connected in series with an inductor Lx, Ly, but the wireless power transfer system 100 may be connected as either in series or parallel for the transmit resonator 102 or the receive resonator 104.

In the exemplary system, a power source Vs is electrically connected with the transmit resonator 102, providing power to the transmit resonator 102. The receive resonator 104 is connected to a load 106. The receive resonator 104 and the load 106 may be connected electrically with a controllable switch (not shown).

In the exemplary embodiment, the transmit resonator 102 includes a coil Lx connected to the power source Vs by a capacitor Cx. The receive resonator 104 includes a coil Ly connected to the load 106 by a capacitor Cy. Inductors Lx and Ly are coupled by a coupling coefficient k. $M_{xy}$ is the mutual inductance between the two coils. The mutual inductance, $M_{xy}$, is related to the coupling coefficient k as shown in the below Equation (1).

$$M_{xy} = k\sqrt{L_x \cdot L_y}. \quad (1)$$

In operation, the transmit resonator 102 transmits wireless power received from the power source Vs. The receive resonator 104 receives the power wirelessly transmitted by the transmit resonator 102, and transmits the received power to the load 106.

Figure 2A:
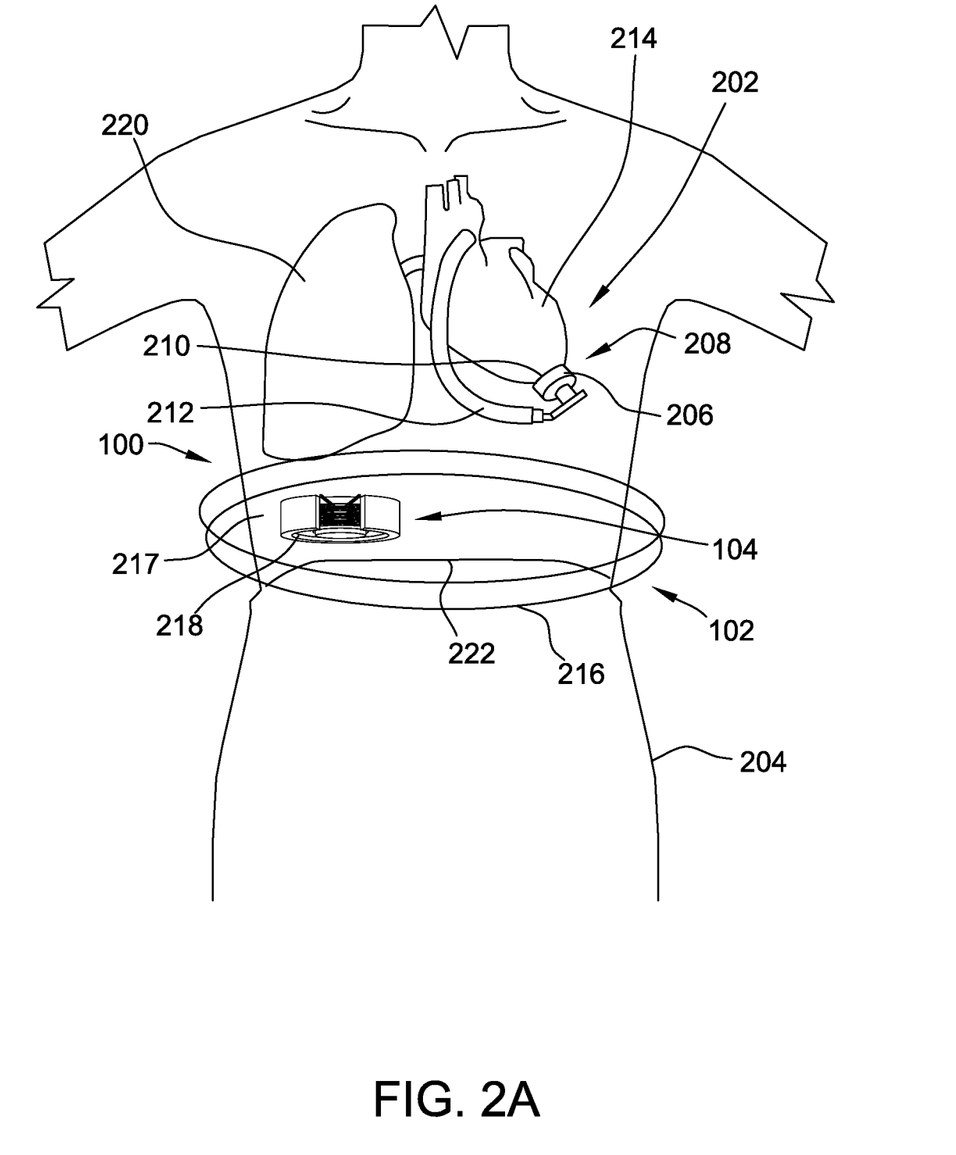
FIG. 2A is an illustration of an exemplary configuration of the wireless power transfer system of FIG. 1 supplying power to a ventricular assist device (VAD).
Figure 2B:
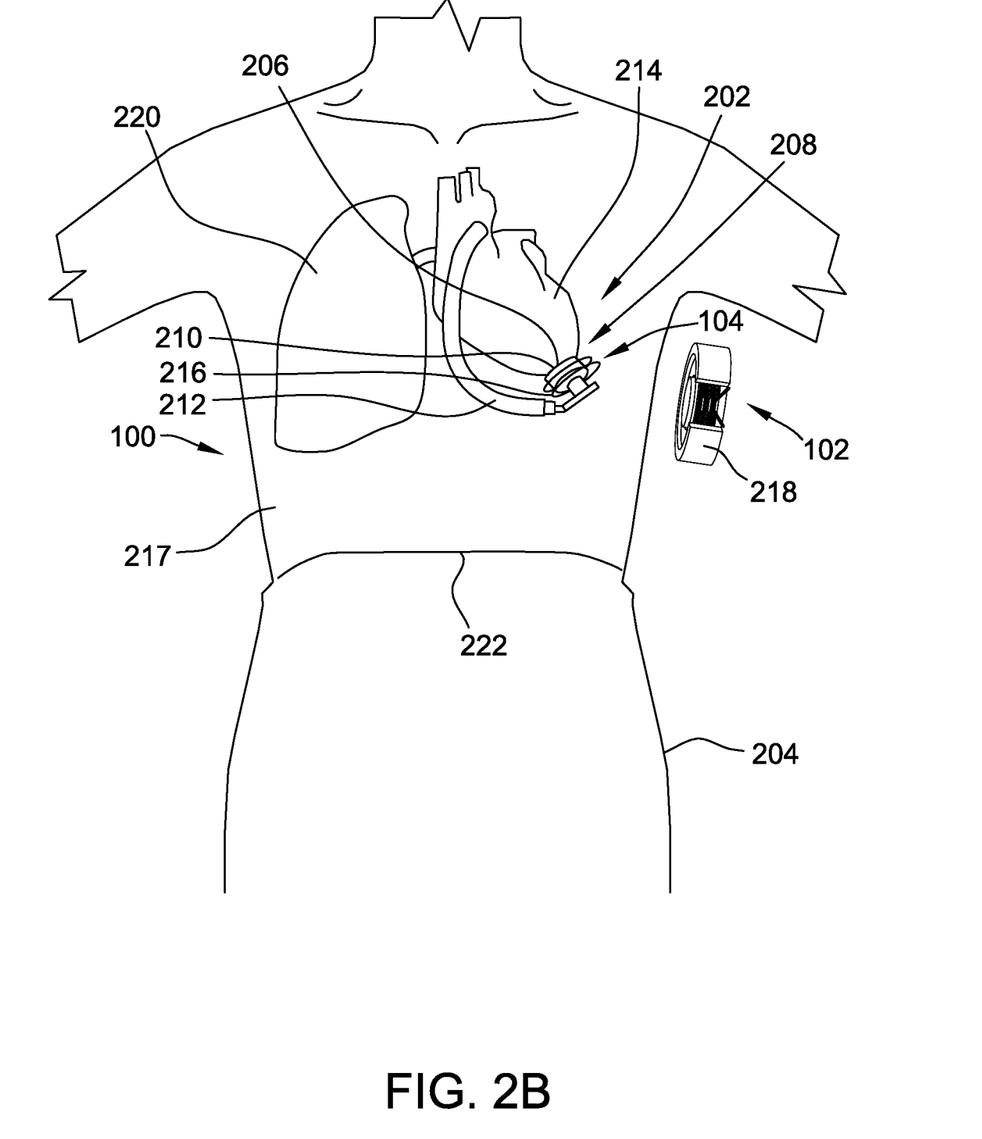
FIG. 2B is an illustration of another exemplary configuration of the wireless power transfer system of FIG. 1 supplying power to a VAD.

FIGS. 2A and 2B illustrate exemplary configurations of using the wireless power transfer system 100 to power a mechanical circulatory support system 202 implanted in a patient's body 204. The mechanical circulatory support system 202 includes an implantable blood pump assembly 206 that includes a blood pump 208, a ventricular cuff 210, and an outflow cannula 212. The receive resonator 104 supplies power to the blood pump assembly 206.

The blood pump assembly 206 can be implemented within a ventricular assist device (VAD) attached to an apex of the left ventricle, as illustrated, the right ventricle, or both ventricles of the heart 214. The blood pump assembly 206 can be attached to the heart 214 via the ventricular cuff 210 which is sewn to the heart 214 and coupled to the blood pump assembly 206. The other end of the blood pump assembly 206 connects to the ascending or descending aorta via an outflow cannula 212 so that the blood pump assembly 206 effectively diverts blood from the weakened ventricle and propels it to the aorta through the outflow cannula 212 for circulation to the rest of the patient's vascular system.

One of the challenges in a power transfer system for a VAD is dispersing heat generated by the implanted modules. For example, an implanted coil placed in the pectoral region may have a heat budget of approximately 0.4 W that, if exceeded, would result in a temperature rise of more than 2° C. Electrical engineering designs for implantable coil modules, however, tend to disperse more heat than 0.4 W in the coil windings alone. For example, additional heat is generated by the rectification of alternating current (AC) to direct current (DC), and by various electronics, microcontrollers, and digital signal processors in the transcutaneous energy transfer system (TETS). Abdominal implant locations can better manage heat, due to a relatively high perfusion in the surrounding tissue, but still may not be acceptable considering the amount of heat emitted from the implanted modules. Further, abdominal placements may be undesirable from a surgical point of view, as a relatively complicated surgery (e.g., tunneling through the diaphragm) may be needed to implant the receive resonator in the patient's abdomen.

Accordingly, in the illustrated embodiment, to facilitate heat management, the receive resonator 104 is positioned in a thoracic cavity 217 of the patient. In some embodiments, the receive resonator 104 is positioned below the lung 220 of the patient and above the diaphragm 222. Alternatively, the receive resonator 104 may be implanted on the top of the diaphragm 222. As a result, the receive resonator 104 is generally in thermal contact with the lung 220, and the heat is dissipated through pulmonary circulation.

The receive resonator 104 may include one or more loops of Litz wire 216 or a plurality of stacked plates 218. For example, in some embodiments, the transmit resonator 102 includes one or more loops of Litz wire 216 and the receive resonator 104 includes a plurality of stacked plates 218. Alternatively, the receive resonator 104 includes one or more loops of Litz wire 216 and the transmit resonator 102 includes a plurality of stacked plates 218. In yet another example, the transmit resonator 102 and the receive resonator 104 may both include one or more loops of Litz wire 216 or both include a plurality of stacked plates 218.

Figure 5:
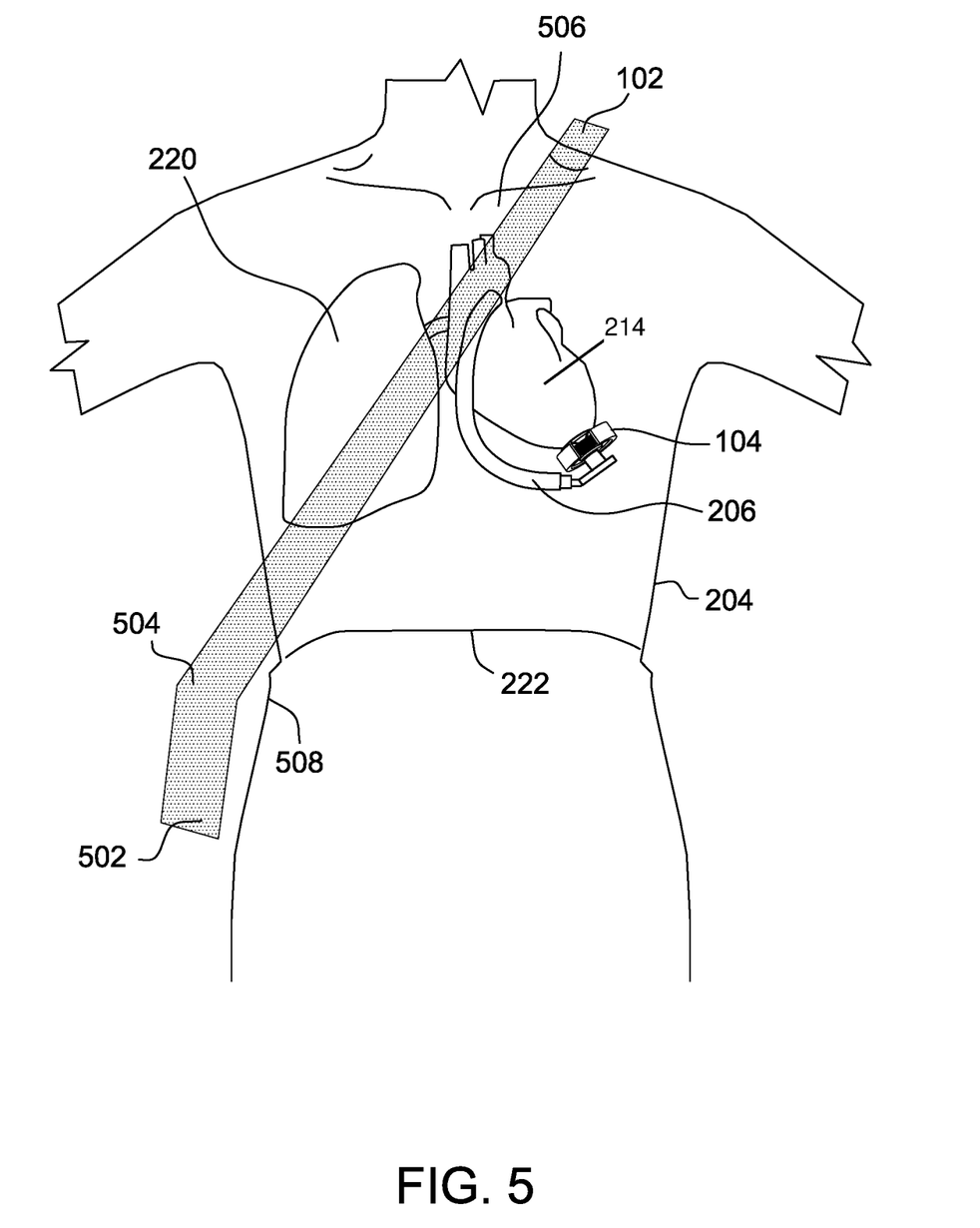
FIG. 5 is schematic diagram of another exemplary configuration of the wireless power transfer system of FIG. 1 supplying power to a VAD.

In some embodiments, the receive resonator 104 is coupled to the blood pump assembly 206 (as shown in FIGS. 2B and 5). For example, one or more loops of Litz wire 216 included in the receive resonator 104 may wrap around the ventricular cuff 210 (shown in FIG. 2B). In an alternative configuration (shown in FIG. 5), a plurality of stacked plates 218 included in receive resonator 104 may be coupled to the blood pump 208, with the ventricular cuff 210 extending through an aperture defined by the stacked plates 218. In these configurations, the receive resonator 104 is in thermal contact with the blood pump assembly 206, and heat is dissipated through the aortic flow through the blood pump assembly 206.

In the exemplary embodiment, the wireless power transfer system 100 may be a hybrid system in which the transmit resonator 102 is one of i) one or more loops of Litz wire 216 or ii) a plurality of stacked plates 218, and the receive resonator 104 is the other of i) the one or more loops of Litz wire 216 or ii) the plurality of stacked plates 218. For example, the FIG. 2A configuration shows the transmit resonator 102 including the loops of Litz wire 216 and the receive resonator 104 including the stacked plates 218. In contrast, the FIG. 2B configuration shows the transmit resonator 102 including the stacked plates 218 and the receive resonator 104 including the loops of Litz wire 216. In general, the geometry of the loops of Litz wire 216 is relatively easy to modify and therefore, the loops of Litz wire 216 can be wrapped around the patient's body 204 (as shown in FIG. 2B), or onto the blood pump assembly 206 (as shown in FIG. 2A). In comparison, a resonator including stacked plates 218 may have a higher power transfer efficiency than a resonator including Litz wire 216. Therefore, a hybrid wireless power transfer system that uses one of each type of resonator realizes the benefits from both types of resonators.

In operation, the transmit and receive resonators 102, 104 are positioned proximate to each other. For example, when the receive resonator 104 is placed in a thoracic cavity 217 of the patient, the transmit resonator 102 may be placed on the side of the patient's chest area or wrapped around the patient's chest area.

Figure 3A:
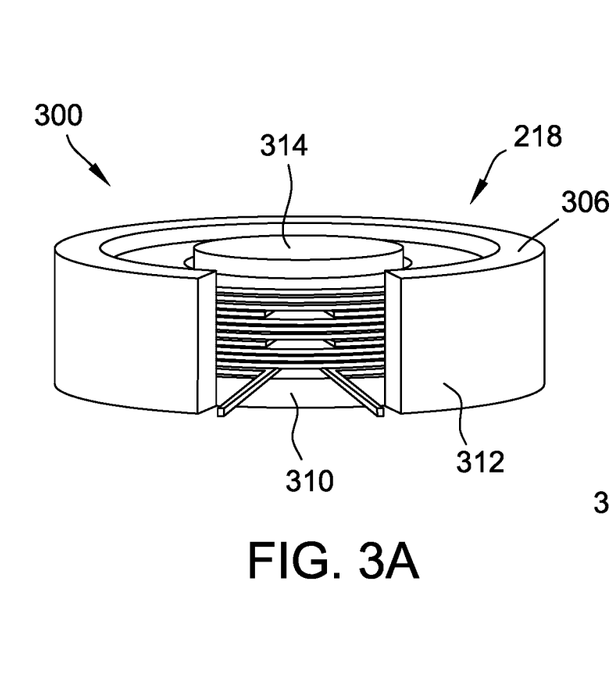
FIG. 3A is a schematic diagram of a resonator having stacked plates.
Figure 3B:
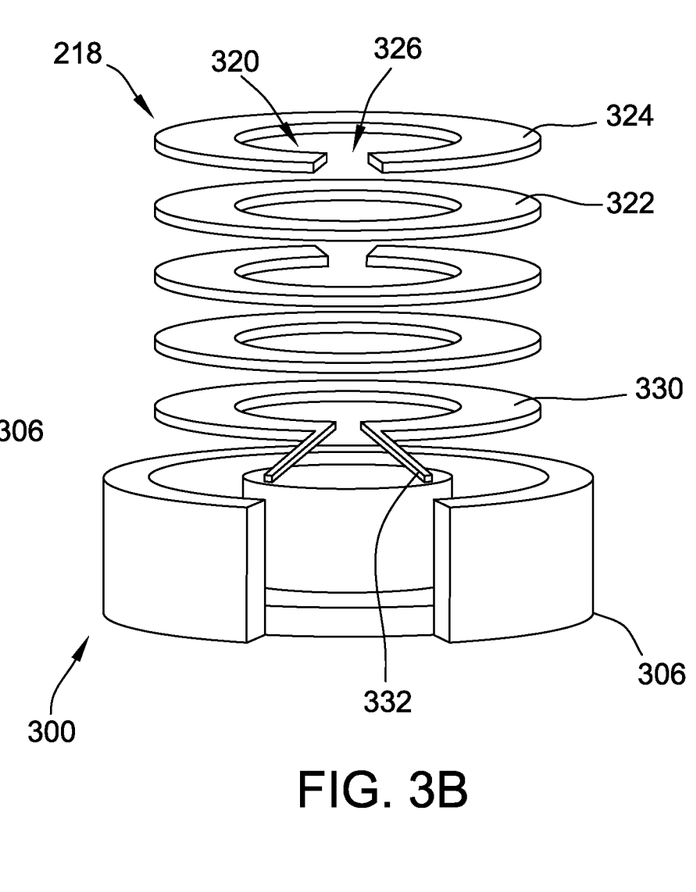
FIG. 3B is an exploded view of the resonator shown in FIG. 3A.

FIG. 3A is a schematic diagram showing the structure of a resonator 102, 104 that is a stacked plate resonator 300 including a plurality of stacked plates 218. FIG. 3B is an exploded view of the stacked plate resonator 300 shown in FIG. 3A. Similar stacked plate resonators are shown and described in "Thin Self-Resonant Structures with a High-Q for Wireless Power Transfer" by Stein et al., Mar. 4, 2018, Thayer School of Engineering, Dartmouth College, Hanover, NH. For clarity, the thickness of stacked plates 218 is exaggerated. In practice, the thickness of each of stacked plates 218 may be in a range from 10 micrometers (μm) to 200 μm (e.g., more particularly, the thickness may in a range from 20-70 μm), and many layers are used in the stacked plate resonator 300. Those of skill in the art will appreciate that the stacked plate resonator 300 may include any suitable number of stacked plates 218. The stacked plates 218 may be stacked into a magnetic core 306.

The magnetic core 306 includes a base 310, a perimeter wall 312, and a post 314. As shown in FIGS. 3A and 3B, each stacked plate 302 includes an aperture 320 sized to receive the post 314, such that each stacked plate 218 generally surrounds the post 314 and is positioned between the post 314 and the perimeter wall 312 of the magnetic core 306.

The stacked plates 218 include a plurality of alternating dielectric layers 322 and conductive layers 324 that form a stack. In the embodiment shown in FIGS. 3A and 3B, each dielectric layer 322 is an annular plate that is generally o-shaped, and extends between an inner diameter and an outer diameter. Each conductive layer 324 defines a notch 326, such that each conductive layer is generally c-shaped and extends between an inner diameter and an outer diameter. Each conductive layer 324 extends circumferentially through an angle (referred to herein as an "angular span") that is less than 360° to define the notch 326.

Further, each conductive layer 324 has an opposite orientation relative to the next conductive layer 324, such that the notches 326 in consecutive conductive layers 324 are oriented at 1800 relative to each other. The opposite orientations result in consecutive conductive layers 324 forming two capacitors.

In one embodiment, one conductive layer 324 is a base conductive layer 330 that includes two terminals 332. The terminals 332 enable the stacked plate resonator 300 to be coupled to, for example, a power source (when functioning as a transmit resonator) or the load 106 (when functioning as a receive resonator). Further, in some embodiments, the stacked plates 218 that form the top and bottom of the stack are conductive layers 324, not dielectric layers 322. Alternatively, a dielectric layer 322 may be positioned on the top and/or bottom of the stack.

In operation, when power is supplied to the stacked plate resonator 300 operating as a transmit resonator or power is received in the stacked plate resonator 300 operating as a receive resonator, current flows through the capacitors formed by the conductive layers 324, creating an inductive current loop. Specifically, the stacked plate resonator 300 functions as a parallel LC resonator, and is capable of wirelessly transmitting power to a receive resonator 104 or wirelessly receiving power from a transmit resonator 102.

The resonance frequency of the stacked plate resonator 300 may be, for example, approximately 6.78 Megahertz (MHz). Specifically, the resonance frequency of the stacked plate resonator 300 is inversely proportional to the square root of the product of inductance and capacitance in the stacked plate resonator 300. The inductance and capacitance are determined based on the design of the stacked plate resonator 300. Accordingly, by modifying the design of the stacked plate resonator 300, the resonance frequency may be modified.

The resonance frequencies of the transmit and receive resonators 102, 104 need to overlap for the wireless power transfer system 100 to function. The resonance frequency of a resonator including loops of Litz wire is generally up to 2.8 MHz and the resonance frequency of a resonator including stacked plates may be approximately 6.78 MHz. Further, the resonance frequency of a resonator 102, 104 is inversely proportional to the square root of the product of inductance and capacitance in the resonator 102, 104, and the inductance is proportional to the coil diameter. For a resonator 102, 104 that includes stacked plates, the capacitance is proportional to plate area. If the radial width of the plates is kept the same, the capacitance is also proportional to the coil diameter. In embodiments where the stacked plates 218 encircle the blood pump assembly 206, the coil diameter of the stacked plates 218 is increased such that the resonance frequency of the stacked plates 218 is in the upper range of the resonance frequency for loops of Litz wire 216. To further facilitate resonance frequency overlap, the capacitance between stacked plates 218 may be modified by adjusting the dielectric constant of the material of the dielectric layers 322 or adjusting the thickness of the dielectric layers 322.

The wireless power transfer system 100 may further include an implantable battery module 402 electrically connected to the blood pump assembly 206. FIGS. 4A-4D are schematic diagrams of exemplary configurations of the receive resonator 104, the battery module 402, and the blood pump assembly 206. In these embodiments, a first electrical cable 404 and a second electrical cable 406 may be used to provide the electrical connections. In FIGS. 4A-4D, a receive resonator 104 including one or more loops of Litz wire 216 is used as an example. Those of skill in the art will appreciate that a receive resonator 104 including a plurality of stacked plates 218 may be used instead and connected similarly to the battery module 402 and the blood pump assembly 206.

Figure 4A:
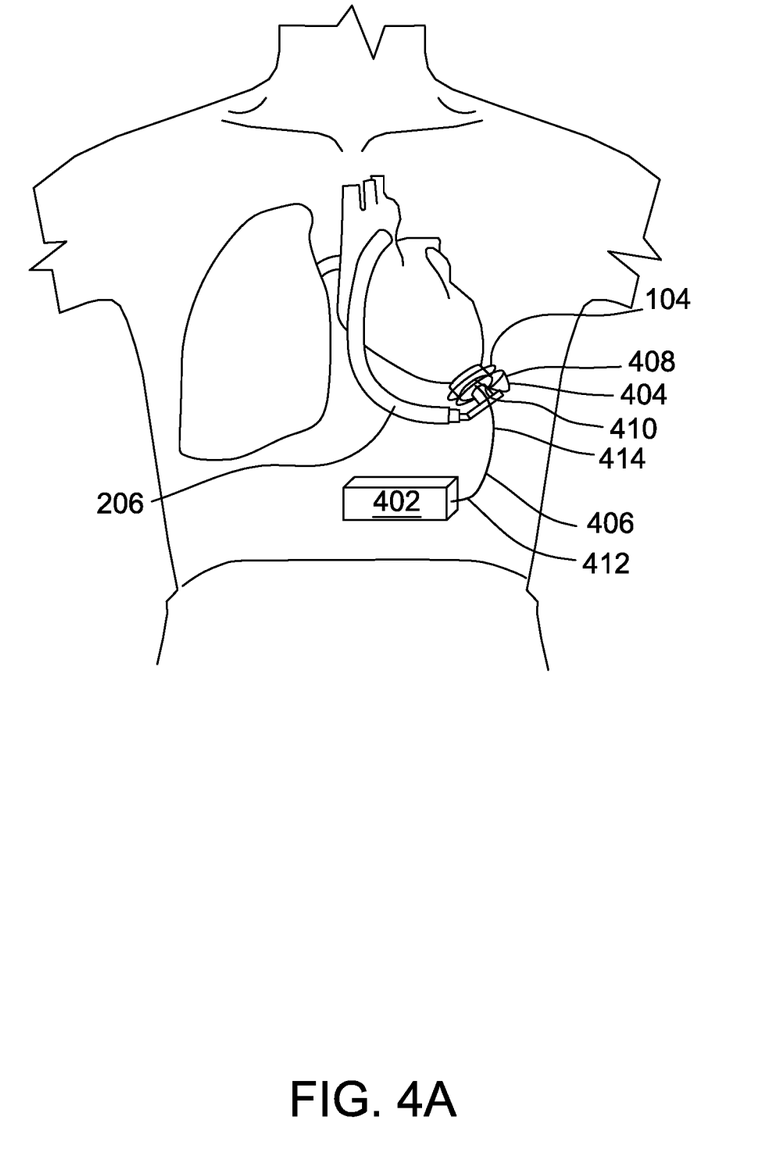
FIG. 4A is a schematic diagram showing an exemplary configuration of the wireless power transfer system of FIG. 1 electrically connected with a VAD and a battery module.
Figure 4B:
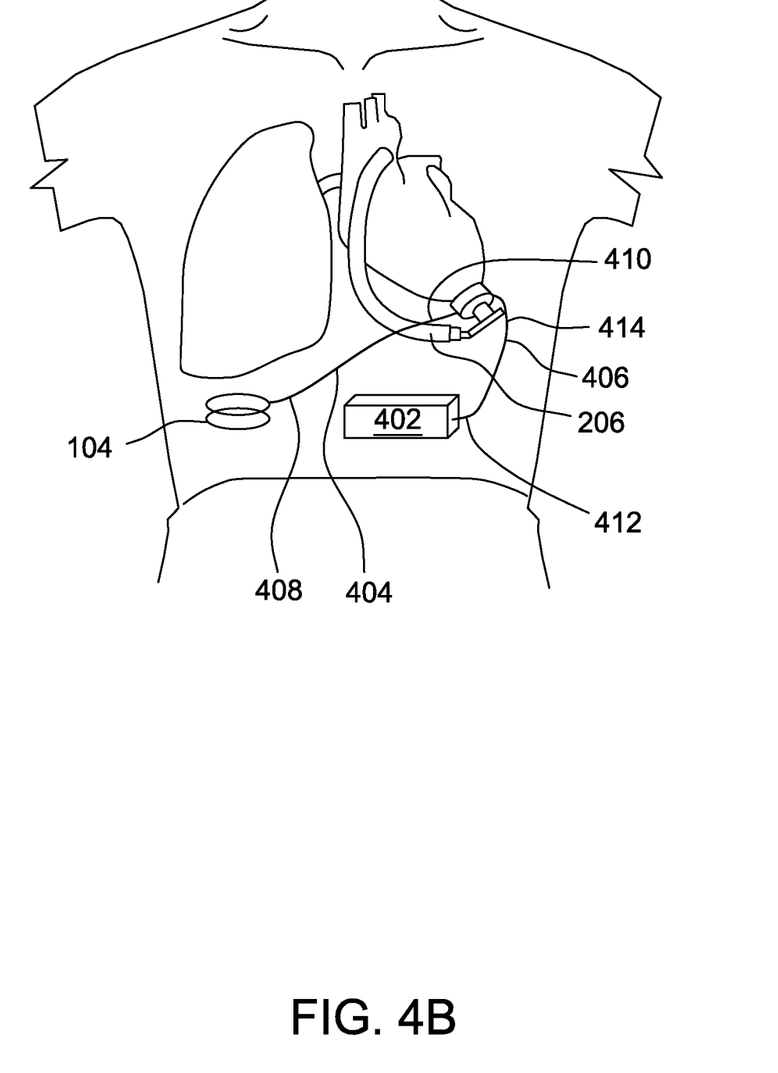
FIG. 4B is a schematic diagram showing another exemplary configuration of the wireless power transfer system of FIG. 1 electrically connected with a VAD and a battery module.

In FIGS. 4A and 4B, the receive resonator 104 is electrically connected directly to the blood pump assembly 206 using the first electrical cable 404. As such, the receive resonator 104 and the battery module 402 both are capable of directly supplying power to the blood pump assembly 206 and may serve as backup for each other. For example, the receive resonator 104 is electrically connected to the blood pump assembly 206 via the first electrical cable 404 with a first end 408 of the first electrical cable 404 connected to the receive resonator 104 and a second end 410 of the first electrical cable 404 connected to the blood pump assembly 206. The battery module 402 is electrically connected to the blood pump assembly 206 via the second electrical cable 406 with a first end 412 of the second electrical cable 406 connected to the battery module 402 and a second end 414 of the second electrical cable 406 connected to the blood pump assembly 206.

Figure 4C:
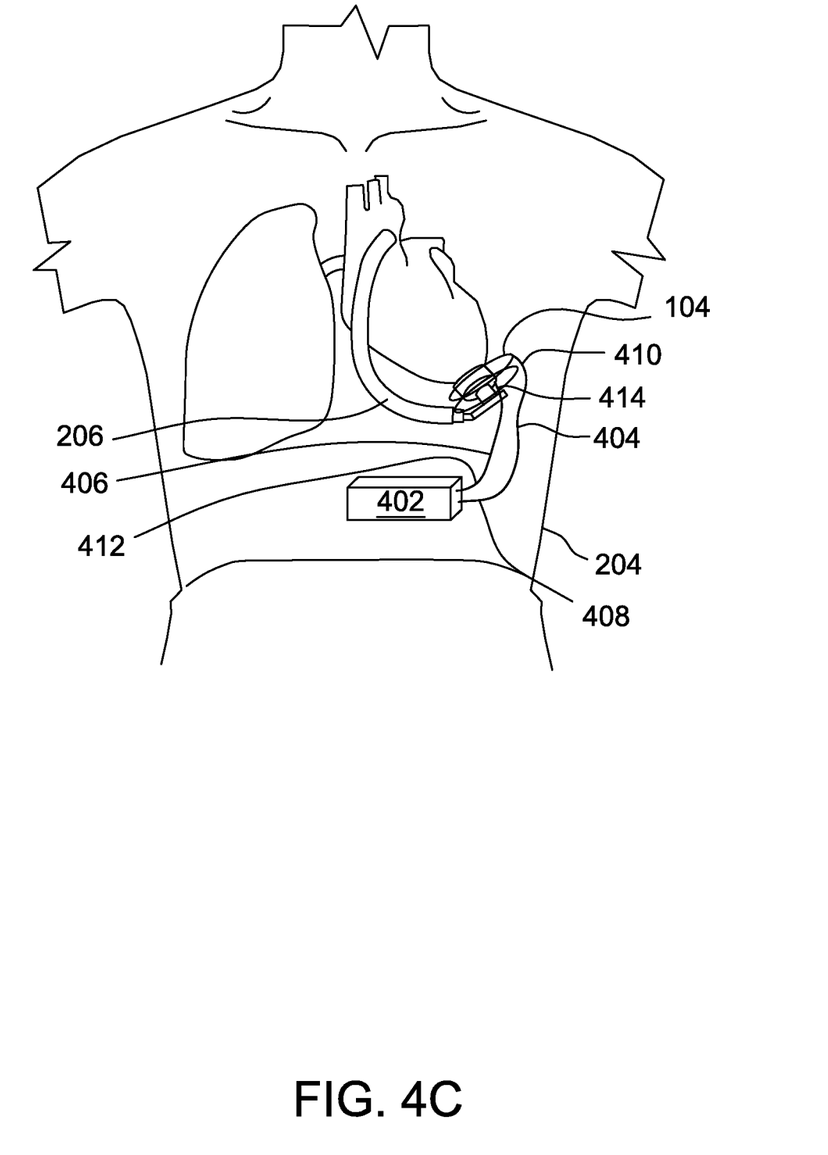
FIG. 4C is a schematic diagram showing another exemplary configuration of the wireless power transfer system of FIG. 1 electrically connected with a VAD and a battery module.
Figure 4D:
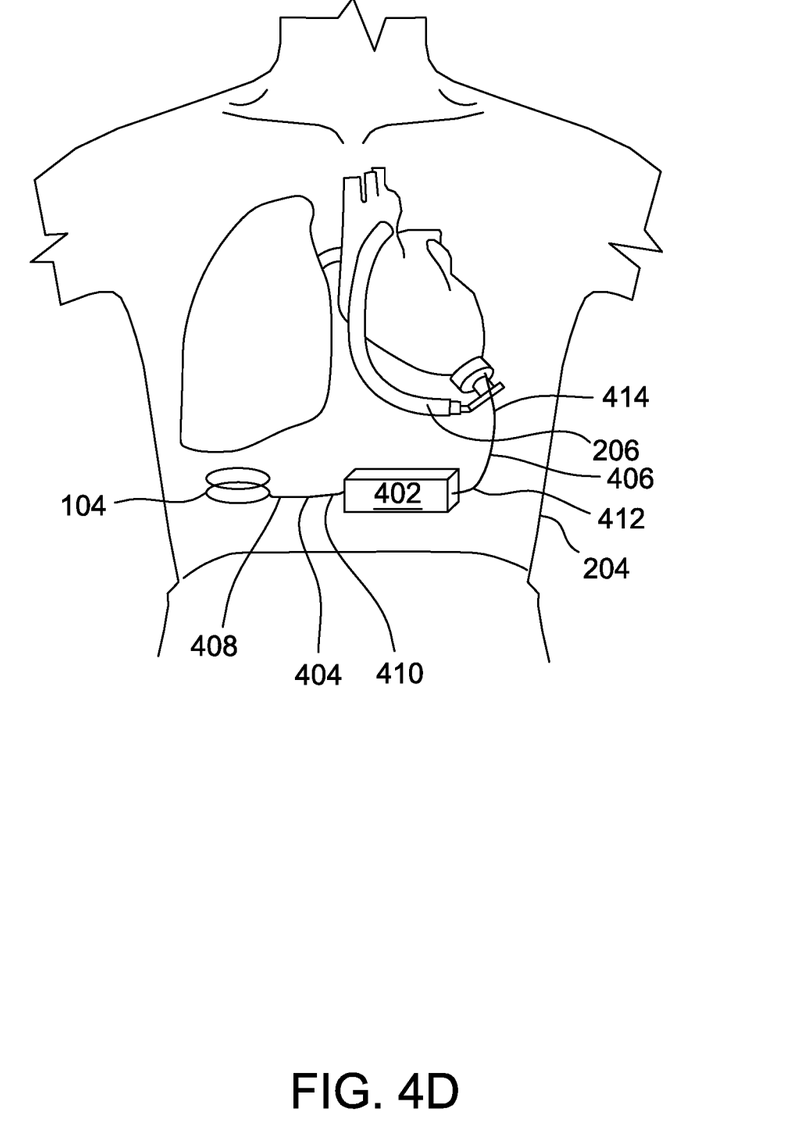
FIG. 4D is a schematic diagram showing another exemplary configuration of the wireless power transfer system of FIG. 1 electrically connected with a VAD and a battery module.

In FIGS. 4C and 4D, the battery module 402 is electrically connected between the receive resonator 104 and the blood pump assembly 206. For example, the battery module 402 is electrically connected to the receive resonator 104 via the first electrical cable 404 with the first end 408 of the first electrical cable 404 connected to the receive resonator 104 and the second end 410 of the first electrical cable 404 connected to the battery module 402. The battery module 402 is also electrically connected to the blood pump assembly 206 via the second electrical cable 406 with the first end 412 of the second electrical cable 406 connected to the battery module 402 and the second end 414 of the second electrical cable 406 connected to the blood pump assembly 206.

FIG. 5 shows another configuration of the wireless power transfer system 100 supplying power to a VAD. In this embodiment, the transmit resonator 102 includes one or more loops of Litz wire 216 (shown in FIG. 2A), and the receive resonator 104 of the wireless power transfer system 100 includes stacked plates 218 (shown in FIG. 2A). The receive resonator 104 is placed proximate the blood pump assembly 206. The receive resonator 104 may also be placed under the lung 220 and above the diaphragm 222. The wireless power transfer system 100 further includes a hub 502 formed integrally with the transmit resonator 102. The hub 502 and the transmit resonator 102 may be included inside a wearable accessory 504. The wearable accessory 504 may be, for example, a messenger bag. Accordingly, the transmit resonator 102 is configured to wrap around the patient's body 204 from the patient's shoulder 506 to the patient's hip 508 on the opposite side. For example, if the receive resonator 104 is positioned at or near left ventricular apex of the heart 214, optimally, the wearable accessory 504 is worn from the left shoulder to the right hip. In some embodiments, the wearable accessory 504 may include structural, non-magnetic components, such as plastic pins or a plastic mesh, that stiffen the wearable accessory 504 against twisting. It may be desirable to prevent the wearable accessory 504 from twisting into a figure eight, because the magnetic field of the transmit resonator 102 may be partially cancelled out in such a configuration. The stiffening components still allow the wearable accessory 504 to flex slightly. That is, if the wearable accessory 504 is considered to as an ellipse, the major and minor axes lengths of the ellipse are allowed to vary for comfort.

In the exemplary embodiment, the hub 502 may include a power converter (not shown) configured to convert power from a power supply to power the transmit resonator 102. The power converter may include an inverter that takes a DC power and converts to an AC power at the operating frequency of the wireless power transfer system 100. The DC power may come from external batteries. The hub may optionally include a converter to convert an AC power from a wall outlet to a DC power having the same DC voltage as the battery provides. Alternatively, the power converter may be located in a different component, such as a power module separate from the hub 502.

Figure 6:
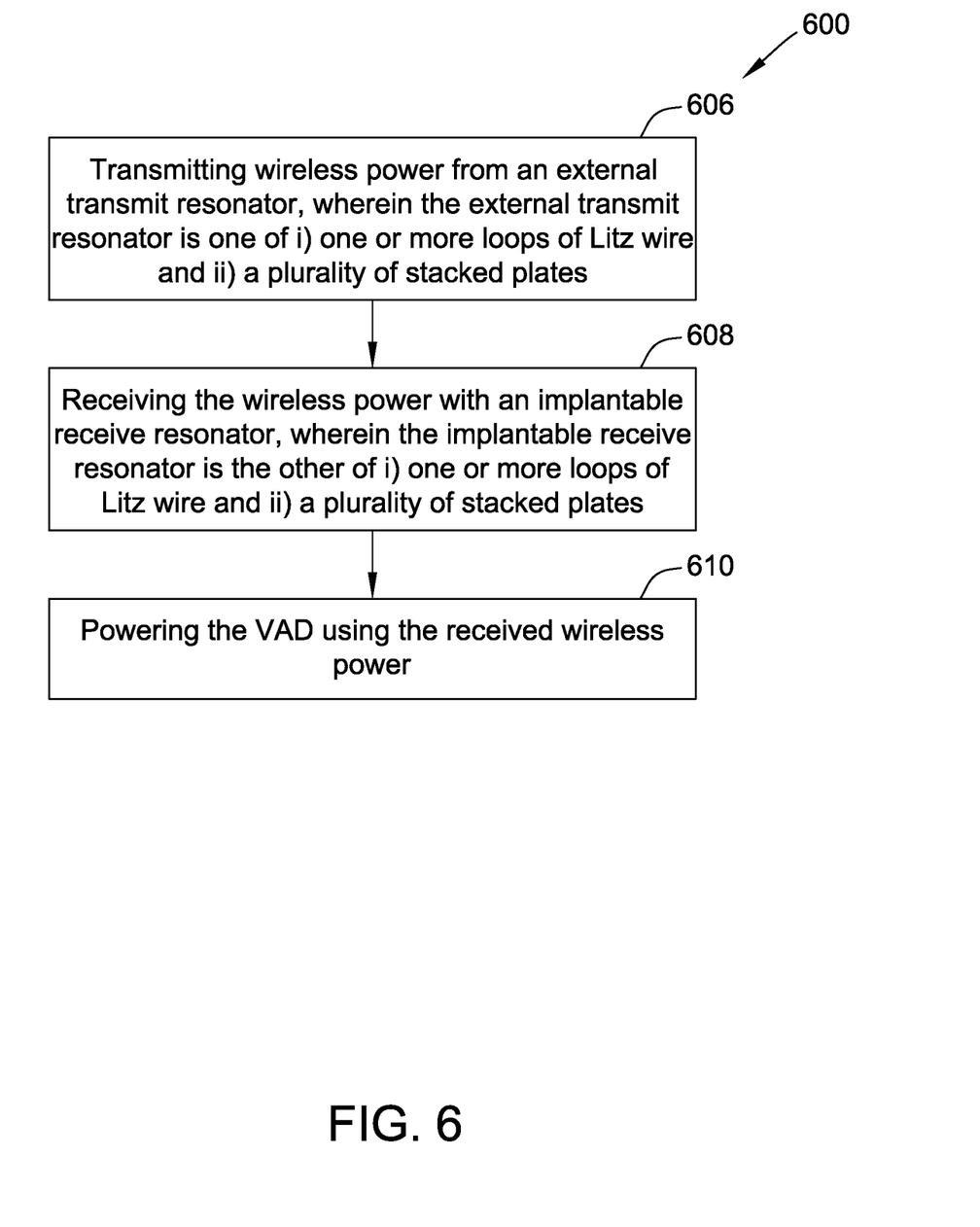
FIG. 6 is a flow chart of an exemplary method of transmitting wireless power.

FIG. 6 is a flow chart of an exemplary method 600 of transmitting wireless power. The method 600 includes transmitting 606 wireless power from an external transmit resonator to an implantable receive resonator, wherein the external transmit resonator includes one of i) one or more loops of Litz wire and ii) a plurality of stacked plates. The method 600 further includes receiving 608 the wireless power with the implantable receive resonator, wherein the implantable receive resonator includes the other of i) the one or more loops of Litz wire and ii) the plurality of stacked plates. Moreover, the method 600 includes powering 610 the VAD using the received wireless power.

Figure 7:
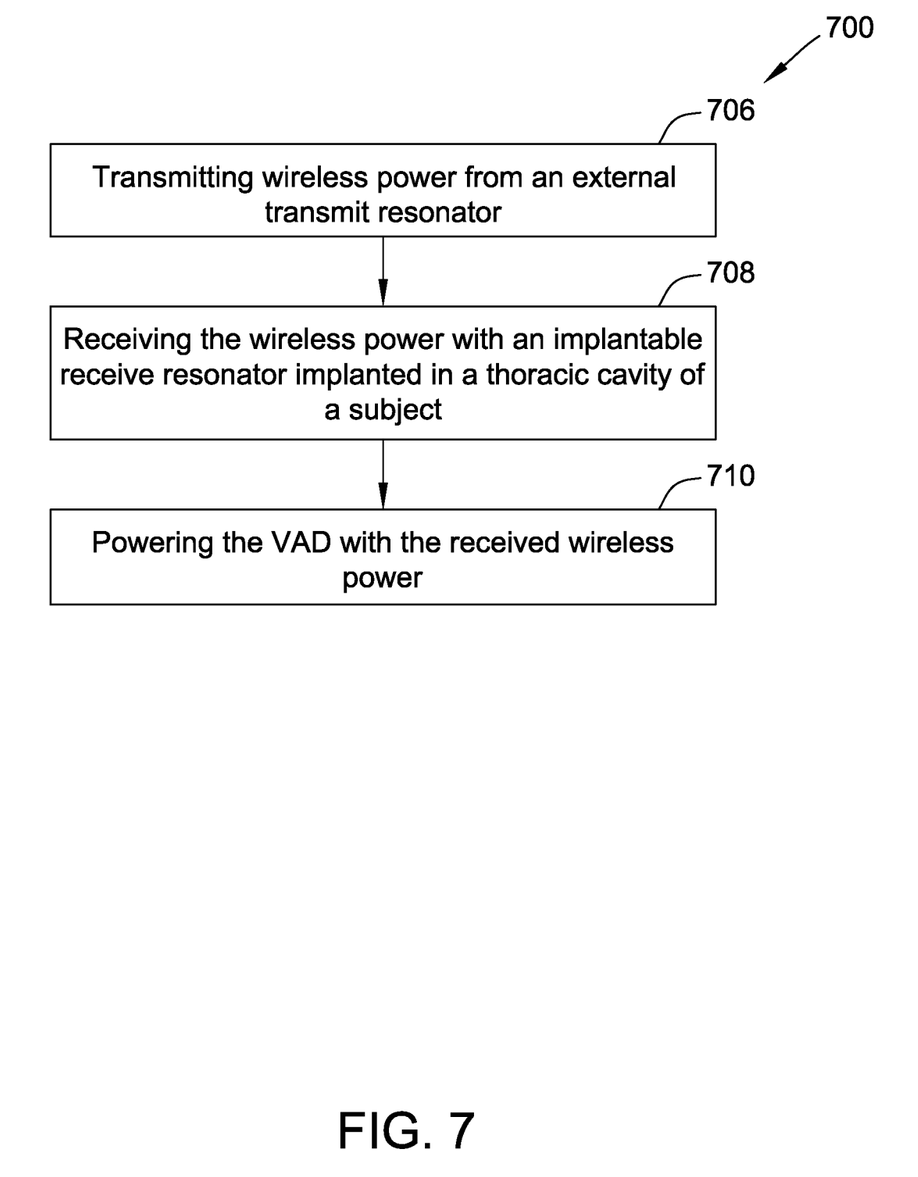
FIG. 7 is a flow chart of another exemplary method of transmitting wireless power.

FIG. 7 is a flow chart of another exemplary method 700 of transmitting wireless power. The method 700 includes transmitting 706 wireless power from an external transmit resonator to an implantable receive resonator. The method 700 further includes receiving 708 the wireless power with the implantable receive resonator implanted in a thoracic cavity of a subject implanted with a VAD. In addition, the method 700 includes powering 710 the VAD using the received wireless power.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A wireless power transfer system, comprising:
a ventricular assist device (VAD) implantable in a subject and comprising a pump that includes a ventricular cuff;
an external transmit resonator configured to transmit wireless power, wherein the external transmit resonator comprises one or more loops of Litz wire; and
an implantable receive resonator configured to receive the transmitted wireless power from the external transmit resonator, wherein the implantable receive resonator is configured to power the VAD using the received wireless power, wherein the implantable receive resonator comprises a plurality of stacked plates, wherein the implantable receive resonator is positioned proximate the pump of the VAD such that the ventricular cuff of the pump extends through an aperture defined by the plurality of stacked plates, and wherein the implantable receive resonator is in thermal contact with the pump to dissipate heat through the pump.

2. The wireless power transfer system of claim 1, wherein the one or more loops of Litz wire are configured to wrap around an upper body of the subject.

3. The wireless power transfer system of claim 2, wherein the external transmit resonator is configured to diagonally wrap around an upper body of the subject from a shoulder of the subject to a hip of the subject.

4. The wireless power transfer system of claim 1, further comprising a hub formed integrally with the external transmit resonator, wherein the hub comprises a power converter configured to convert a first power provided by a power source to a second power received by the external transmit resonator.

5. The wireless power transfer system of claim 1, wherein the plurality of stacked plates are sized such that a resonance frequency of the implantable receive resonator overlaps with a resonance frequency range of the external transmit resonator.

6. The wireless power transfer system of claim 5, wherein the implantable receive resonator is configured to be implanted below a lung of the subject and above a diaphragm of the subject.

7. The wireless power transfer system of claim 1, further comprising an implantable battery module configured to be electrically connected to the VAD.

8. The wireless power transfer system of claim 7, wherein the implantable battery module is configured to be electrically connected between the implantable receive resonator and the VAD, and wherein the implantable receive resonator is configured to power the VAD by charging the implantable battery.

9. The wireless power transfer system of claim 7, wherein the implantable receive resonator is configured to be electrically connected directly to the VAD.

10. A method of transmitting wireless power, comprising:
    transmitting wireless power from an external transmit resonator to an implantable receive resonator, wherein the external transmit resonator includes one or more loops of Litz wire;
    receiving the wireless power at the implantable receive resonator, wherein the implantable receive resonator includes a plurality of stacked plates; and
    powering a ventricular assist device (VAD), implantable in a subject and comprising a pump that includes a ventricular cuff, using the received wireless power, wherein the implantable receive resonator is positioned proximate the pump of the VAD such that the ventricular cuff of the pump extends through an aperture defined by the plurality of stacked plates, and wherein the implantable receiver resonator is in thermal contact with the pump to dissipate heat through the pump.

11. The method of claim 10, wherein transmitting wireless power further comprises transmitting wireless power from the external transmit resonator configured to wrap around an upper body of a subject.

12. The method of claim 11, wherein transmitting wireless power further comprises transmitting wireless power from an external transmit resonator configured to wrap diagonally around an upper body of the subject from a shoulder of the subject to a hip of the subject.

13. The method of claim 10, wherein the plurality of stacked plates are sized such that a resonance frequency of the implantable receive resonator overlaps with a resonance frequency range of the external transmit resonator.

14. The method of claim 10, wherein receiving the wireless power further comprises receiving the wireless power at an implantable receive resonator implanted below a lung of a subject and above a diaphragm of the subject.

15. The method of claim 10, further comprising electrically connecting an implantable battery module to the VAD.

16. The method of claim 15, further comprising electrically connecting the implantable battery module between the implantable receive resonator and the VAD.

17. The method of claim 15, further comprising electrically connecting the implantable receive resonator directly to the VAD.

* * * * *